(12) United States Patent
Muhuri et al.

(10) Patent No.: US 10,016,374 B2
(45) Date of Patent: Jul. 10, 2018

(54) DISINTEGRANT FREE COMPOSITION OF CINACALCET

(71) Applicant: JUBILANT GENERICS LIMITED, Uttar Pradesh (IN)

(72) Inventors: Goutam Muhuri, Basking Ridge, NJ (US); Ravikumar Nithiyanandam, Tamil Nadu (IN); Ganesh Vinayak Gat, Pune (IN); Swati Mukherjee, Haryana (IN); Bharat Bhushan, Haryana (IN)

(73) Assignee: Jubilant Generics Limited, Uttar Pradesh (IN)

( * ) Notice: Subject to any disclaimer, the term of this patent is extended or adjusted under 35 U.S.C. 154(b) by 0 days.

(21) Appl. No.: 14/901,160

(22) PCT Filed: Jun. 26, 2014

(86) PCT No.: PCT/IB2014/062620
§ 371 (c)(1),
(2) Date: Dec. 28, 2015

(87) PCT Pub. No.: WO2014/207691
PCT Pub. Date: Dec. 31, 2014

(65) Prior Publication Data
US 2016/0143863 A1 May 26, 2016

(30) Foreign Application Priority Data
Jun. 26, 2013 (IN) .......................... 1898/DEL/2013

(51) Int. Cl.
*A61K 31/137* (2006.01)
*A61K 9/20* (2006.01)
*A61K 9/48* (2006.01)

(52) U.S. Cl.
CPC .......... *A61K 31/137* (2013.01); *A61K 9/2054* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |
| 7,829,595 B2 * | 11/2010 | Lawrence ............ | A61K 9/2077 514/579 |
| 2008/0181959 A1 * | 7/2008 | Zalit ..................... | A61K 9/146 424/489 |
| 2010/0168247 A1 | 7/2010 | Zalit et al. | |
| 2011/0287065 A1 * | 11/2011 | Neville ................... | A61K 9/10 424/400 |
| 2012/0009258 A1 | 1/2012 | Rimkus et al. | |
| 2012/0270949 A1 | 10/2012 | Paetz et al. | |

FOREIGN PATENT DOCUMENTS

| | | |
|---|---|---|
| WO | 2008064202 A2 | 11/2007 |
| WO | 2010086129 A1 | 8/2010 |
| WO | 2012071535 A2 | 5/2012 |

OTHER PUBLICATIONS www.drugs.com (accessed Mar. 3, 2017).*
"Disintegrants for Normal Tablets", Pharmaceutical Technology of BASF Excipients—BASF the Chemical Company, Jun. 2008, 3rd revision, section 1.2, pp. 22-25.
"Povidone; Soluble Kollidon Grades" Pharmaceutical Technology of BASF Excipients—BASF the Chemical Company, Jun. 2008, 3rd revision, section 1.4, p. 30.

* cited by examiner

*Primary Examiner* — Craig D Ricci
(74) *Attorney, Agent, or Firm* — Baker & Hostetler LLP

(57) ABSTRACT

The present invention relates to pharmaceutical composition of Cinacalcet or a pharmaceutically acceptable salt thereof comprising diluents, binders and lubricants, wherein said composition is substantially free of disintegrant. It further relates to process for preparing such compositions.

6 Claims, 1 Drawing Sheet

*In-vitro* dissolution test of pharmaceutical composition of Cinacalcet HCl
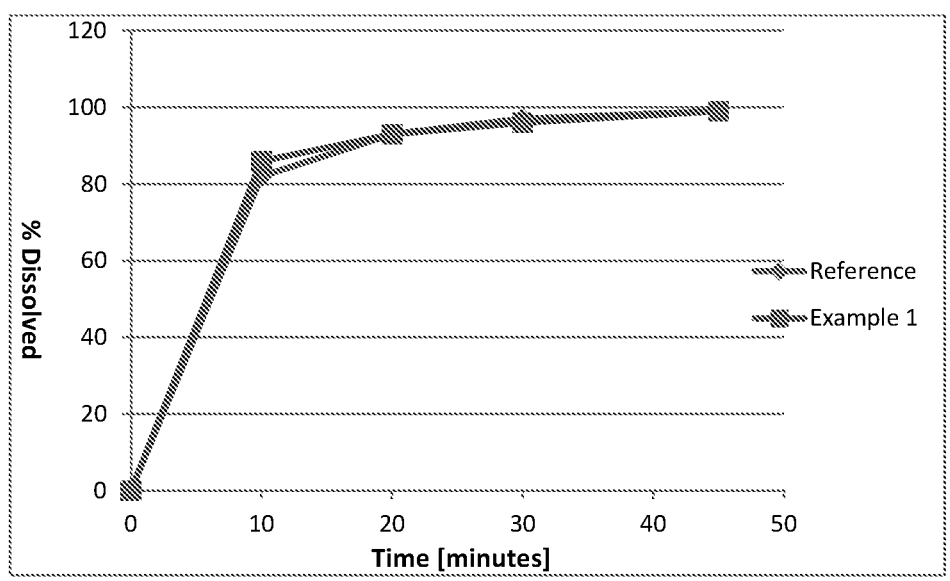

DISINTEGRANT FREE COMPOSITION OF CINACALCET

CROSS REFERENCE TO RELATED APPLICATIONS

This application is a National Stage of International Application No. PCT/IB2014/062620, filed on Jun. 26, 2014, which claims priority to Indian patent application no. 1898/DEL/2013, filed on Jun. 26, 2013, the disclosures of which are incorporated by reference in their entirety.

FIELD OF THE INVENTION

The present invention relates to disintegrant free solid oral pharmaceutical compositions of Cinacalcet or a pharmaceutically acceptable salt thereof. The invention also relates to the process for preparing such compositions.

BACKGROUND OF THE INVENTION

Cinacalcet hydrochloride is chemically known as N-[1-(R)-(–)-(1-naphthyl)ethyl]-3-[3(trifluoromethyl)phenyl]-1-aminopropane hydrochloride and has the following structural formula:

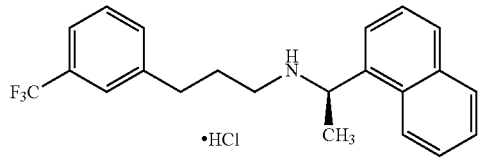 [SMILES: C[C@@H](NCCCc1cccc(C(F)(F)F)c1)c1cccc2ccccc12 ; Cl]

Cinacalcet HCl contains a chiral center and the active substance is the R-enantiomer. It is a white to off-white, non-hygroscopic crystalline powder.

Cinacalcet is a calcimimetic which is used to treat secondary hyperparathyroidism as a consequence of chronic renal failure. In addition, the substance is also used for the treatment of hypercalcaemia in patients with parathyroid carcinoma. The synthesis and clinical utility of Cinacalcet is described in U.S. Pat. Nos. 6,011,068, 6,031,003, 6,211,244 and 6,313,146.

In general, it is desirable to incorporate a disintegrant in a solid oral dosage form of a poorly soluble drug like Cinacalcet. The disintegrating agent plays an important role in the formulation of solid oral dosage forms of poorly soluble compounds by promoting breakup of the solid oral dosage forms into smaller fragments in an aqueous environment thereby increasing the available surface area and in turn promoting a rapid release of the drug substance. The following published patent/patent applications on Cinacalcet solid oral dosage forms have highlighted the use of disintegrating agent in the formulation to attain optimum dissolution profile:

Patent publication U.S. Pat. No. 7,829,595 is listed in the FDA's Orange Book for Cinacalcet film coated tablets. The publication recites that Cinacalcet has a very low solubility in water, i.e, between 0.1 mg/ml and 1.6 mg/ml, depending on the pH value. U.S. Pat. No. 7,829,595 further teaches the use of Cinacalcet HCl compositions comprising: (a) from 10% to 40% by weight of Cinacalcet HCl; (b) from 45% to 85% by weight of at least one diluent; (c) from 1% to 5% by weight of at least one binder; (d) from 1% to 10% by weight of at least one disintegrant; and (e) from 0.05% to 5% by weight of at least one additive chosen from glidants, lubricants, and anti-adherents; wherein the percentage by weight is relative to the total weight of the composition.

US 2010/0168247 refers to a method for preparing a solid composite of Cinacalcet, comprising at least one carrier. Further, use of disintegrant in the amount of 10 to 40% is also disclosed.

WO 2012/071535 discloses hard shell capsules containing a granular powder formulation of Cinacalcet which comprises 1-8% of disintegrant.

Also, other patent publications on Cinacalcet like US 2012/0009258 and US 2012/0270949 disclose use of disintegrant in Cinacalcet formulation.

Disintegrating agents are hygroscopic in nature which may pose formulation challenge with moisture sensitive drugs. Typically, disintegrants like Crospovidone, Sodium Starch Glycolate may contain more than or equal to 5% w/w of water content. Further, use of more than 10% w/w of disintegrant in a formulation may lead to softening of tablets during storage. Also, disintegrants are usually not used in amounts of less than 1%, because of failure to achieve disintegration of the dosage form which may impact release profile.

The objective of the present invention was therefore to overcome the above-mentioned disadvantages.

As Cinacalcet hydrochloride is sparingly soluble in water, its formulation without disintegrant or substantially free of disintegrant is challenging due to possible failure of disintegration of the solid dosage form which may adversely affect dissolution and bioequivalence. Overall, a person skilled in the formulation art may not pursue a dosage form with above challenges.

The present inventors have surprisingly developed a disintegrant free solid oral pharmaceutical composition of Cinacalcet without compromising on dissolution properties of the prepared dosage form. The present invention further provides a simple, economical and industrially feasible process for preparing pharmaceutical composition of Cinacalcet.

SUMMARY OF THE INVENTION

The present invention provides a pharmaceutical composition comprising Cinacalcet or a pharmaceutically acceptable salt thereof, wherein the pharmaceutical composition is free of disintegrant.

In another embodiment of the present invention there is provided a pharmaceutical composition comprising Cinacalcet or a salt thereof, wherein the pharmaceutical composition is substantially free of disintegrant.

In another embodiment of the present invention there is provided a pharmaceutical composition comprising Cinacalcet or a salt thereof, wherein disintegrant is less than 1% w/w by total weight of the composition.

In another embodiment of the present invention there is provided a pharmaceutical composition comprising Cinacalcet or a salt thereof, which further comprises pharmaceutically acceptable excipients like diluent, binder, and lubricant.

In yet another embodiment of the present invention there is provided use of a pharmaceutical composition of the present invention in the manufacture of a medicament for treating secondary hyperparathyroidism, hypercalcemia in patients with parathyroid carcinoma, severe hypercalcemia in patients with primary hyperparathyroidism.

BRIEF DESCRIPTION OF THE DRAWINGS

The above and other objects and features of the present invention will become apparent from the following description of the invention, when taken in conjunction with the accompanying drawing, in which:

FIG. 1 shows a in-vitro dissolution test of pharmaceutical composition of Cinacalcet HCl

DETAILED DESCRIPTION OF THE INVENTION

The present invention is directed to disintegrant free pharmaceutical compositions of Cinacalcet or a pharmaceutically acceptable salt thereof. It further relates to the process for preparing such composition.

Pharmaceutically acceptable salts used are preferably acid addition salts. Examples of suitable salts are, but not limited to, hydrochlorides, carbonates, hydrogen carbonates, acetates, lactates, butyrates, propionates, sulphates, methane sulphonates, citrates, tartrates, nitrates, sulphonates, oxalates and/or succinates. Preferably, pharmaceutically acceptable salt of Cinacalcet is hydrochloride salt.

The compositions of the present invention comprise Cinacalcet or a pharmaceutically acceptable salt thereof having $D_{50}$ less than or equal to about 75 µm. Preferably, the $D_{50}$ ranges from 5 µm to 45 µm. More preferably, the $D_{50}$ ranges from 10 µm to 30 µm. The particle size of Cinacalcet HCl can be measured by techniques such as Laser light scattering (e.g. Malvern Light Scattering). Coulter counter, microscopy and the like.

Cinacalcet is present in an amount ranging from about 1 mg to about 360 mg, for example from about 5 mg to about 240 mg, or from about 20 mg to about 100 mg. In another preferred embodiment, the amount of Cinacalcet in the formulation ranges from 30 mg to 90 mg.

"Disintegrant free pharmaceutical composition" as used herein refers to the pharmaceutical composition of Cinacalcet, which does not contain any disintegrant.

According to a particularly preferred embodiment, the pharmaceutical composition is substantially free of disintegrant. In particular, the pharmaceutical composition comprises less than 1% w/w, more preferably less than 0.6% w/w of a disintegrant, by total weight of the composition.

Various disintegrants include, but are not limited, to croscarmellose sodium, carboxymethyl cellulose sodium, crospovidone, polacrilin potassium, sodium starch glycolate and/or combinations thereof.

The disintegrant free pharmaceutical composition of the present invention further comprises one or more pharmaceutically acceptable excipients selected from the group consisting of diluents, binders, lubricants and anti-adherents.

Pharmaceutically acceptable diluents include microcrystalline cellulose ("MCC"), silicified MCC (e.g., PROSOLV™), microfine cellulose, lactose, starch, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide and mixtures thereof. Preferably, diluent is microcrystalline cellulose or lactose or any combination thereof. Preferably, the amount of diluent is from about 20.0% to about 80.0% w/w. More preferably, the amount of diluent is from about 30.0% to about 70.0% w/w. Most preferably, the amount of diluent is about 40.0% w/w by total weight of the composition.

Pharmaceutically acceptable binders include acacia, guar gum, alginic acid, dextrin, maltodextrin, methylcellulose, ethyl cellulose, hydroxyethyl cellulose, hydroxypropyl cellulose (e.g., KLUCEL®), hydroxypropyl methylcellulose (e.g., METHOCEL®), carboxymethyl cellulose sodium, povidone (various grades of KOLLIDON®, PLASDONE®), starch, pregelatinized starch and mixtures thereof. Preferably, binder is povidone. Preferably, the amount of binder is from about 1.0% to about 8.0% w/w. More preferably, the amount of binder is from about 4.0% to about 7.0% w/w.

Pharmaceutically acceptable lubricants include stearic acid, adipic acid, sodium stearyl fumarate (Pruv®) and/or magnesium stearate. Preferably, lubricant is magnesium stearate. Preferably, the amount of lubricant is from about 0.10% to about 2.0% w/w. More preferably, the amount of lubricant is form about 0.25% to about 1.0% w/w. Most preferably, the amount of lubricant is about 1.0% w/w by total weight of the composition.

Other carrier materials (such as anti-adherents, colorants, flavors, sweeteners and preservatives) that are known in the pharmaceutical art can be included in composition of the present invention.

In another embodiment of the present invention, a pharmaceutical composition comprising:
(a) from about 10 to 60% by weight Cinacalcet or its pharmaceutically acceptable salts;
(b) from about 20.0 to 80.0% by weight of one or more diluents;
(c) from about 1.0% to 8.0% by weight of one or more binders;
wherein the pharmaceutical composition is substantially free of disintegrating agent.

According to one of the embodiment, the disintegrant free pharmaceutical composition of the present invention is in the form of tablets, pills, capsules, lozenges or granules.

The solid pharmaceutical composition of the invention may be prepared by conventional processes known to those of ordinary skill in the art, including, but not limited to, wet granulation, dry granulation such as slugging or compaction, or direct compression of the formulation into tablets or filling into capsules.

The pharmaceutical composition further comprises at least one coating material in an amount ranging from about 1% to about 6% w/w by total weight of the composition.

In further embodiment, pharmaceutical composition of the present invention can be prepared by a process comprising the steps of:
(a) dissolving or dispersing Cinacalcet optionally with a binder in a solvent,
(b) granulating the excipient blend with the solution comprising Cinacalcet,
(c) drying and lubricating the granules, and
(d) compressing the granules into tablets, or alternatively filling into capsules.

For coating, preferably macromolecular substances are used, such as modified celluloses, polymethacrylates, polyvinyl pyrrolidone, polyvinyl acetate phthalate, zein and/or shellac. Hydroxypropyl methyl cellulose is preferably used, especially HPMC with average molecular weight of 10,000 to 150,000 g/mol.

The pharmaceutical composition of the present invention can be used for treatment of secondary hyperparathyroidism (HPT) in patients with chronic kidney disease (CKD) on dialysis; treatment of hypercalcemia in patients with parathyroid carcinoma; treatment of severe hypercalcemia in patients with primary HPT who are unable to undergo parathyroidectomy.

The compositions of the invention may also contain one or more active ingredients in addition to the Cinacalcet. The additional active ingredient may be another calcium receptor-active compound, or it may be an active ingredient having a different therapeutic activity. Examples of such additional active ingredients include, for example, vitamins and their analogs, such as vitamin D and analogs thereof, antibiotics, and cardiovascular agents.

The following non-limiting examples illustrate specific embodiments of the present invention. They are, however, not intended to be limiting the scope of the present invention in any way.

EXAMPLE

Composition of 90 mg Cinacalcet Tablet

TABLE 1

| Ingredients | Function | Composition per tablet (mg) Example 1 |
|---|---|---|
| Cinacalcet Hydrochloride | Drug Substance | 99.181 |
| Microcrystalline Cellulose | Diluent | 411.419 |
| Povidone | Binder | 12 |
| Pregelatinised starch | Binder | 12 |
| Magnesium Stearate | Lubricant | 5.4 |
| Coating | | 18.90 |
| Total | | 558.90 |

Tablets containing Cinacalcet HCl were prepared according to the process as given below:
(a) Cinacalcet and portion of binder were dissolved in water;
(b) Another portion of binder and portion of diluent were mixed to form a blend;
(c) Blend of step (b) was granulated with solution of step (a);
(d) The granules were dried and blended with another portion of diluents;
(e) Blend of step (d) was lubricated by mixing with magnesium stearate;
(f) Lubricated blend of step (e) was compressed into tablets or filled into capsule shell.

Disintegration Characteristics of the Pharmaceutical Composition

The standardized method and equipment for testing of disintegrating time is provided in United State Pharmacopeia (USP). The test (Example 1) and reference formulation of the invention were tested according to the said method.

TABLE 2

Comparative Disintegration Time

| Test Parameter | SENSIPAR ® Tablets 90 mg (Reference) | Example 1 |
|---|---|---|
| Disintegration Time (Minutes) | Less than 2 minutes | Less than 2 minutes |

The in-vitro disintegration time of test Example 1 and reference SENSIPAR® 90 mg film coated tablets formulation is shown in comparative table 2. The test and reference composition exhibited comparable disintegration time.

Dissolution Characteristics of the Pharmaceutical Composition

The standardized method and equipment for testing dissolution time is provided in United States Pharmacopeia (USP). The dissolution profile of Example 1 was measured in 900 ml of 0.05 N HCl in United States Pharmacopeia (USP)—National Formulary (NF) (USP 36/NF 31), chapter 711 using a USP 2 apparatus at a temperature of 37±0.5° C. and a rotation speed of 75 revolutions per minute.

The dissolution test was conducted on the reference formulation SENSIPAR® 90 mg film coated tablets in comparison to a solid oral tablet dosage form prepared according to Example 1. The dissolution profile of the tablets prepared in Example 1 is shown in table 3 and FIG. 1.

TABLE 3

Comparative Dissolution Data

| Time (min) | SENSIPAR ® Tablets 90 mg (Reference) % Drug Dissolved | Example 1 |
|---|---|---|
| 10 | 82 | 86 |
| 20 | 93 | 93 |
| 30 | 97 | 96 |
| 45 | 99 | 99 |

The dissolution data presented in comparative table 3 shows that dissolution profile of the test composition according to the present invention is comparable to the reference SENSIPAR® 90 mg film coated tablets.

The test formulation despite of being free from disintegrating agent exhibited comparable disintegration and dissolution profile in comparison to reference SENSIPAR® 90 mg film coated tablets which contain substantial amount of disintegrating agent.

While several particular forms of the invention have been illustrated and described, it will be apparent that various modifications and combinations of the invention detailed in the text can be made without departing from the spirit and scope of the invention. Accordingly, it is not intended that the invention be limited, except as by the appended claims.

We claim:

1. A disintegrant free, immediate release, solid oral pharmaceutical dosage form of Cinacalcet hydrochloride prepared by a wet granulation process.

2. The pharmaceutical dosage form according to claim 1, further comprising one or more pharmaceutically acceptable excipients selected from one or more of diluents, binders, lubricants, anti-adherents and mixtures thereof.

3. The pharmaceutical dosage form according to claim 2, wherein the one or more diluents comprise microcrystalline cellulose, silicified MCC, microfine cellulose, lactose, starch, mannitol, sorbitol, dextrates, dextrin, maltodextrin, dextrose, calcium carbonate, calcium sulfate, dibasic calcium phosphate dihydrate, tribasic calcium phosphate, magnesium carbonate and magnesium oxide.

4. The pharmaceutical dosage form according to claim 2, wherein the one or more binders comprise acacia, guar gum, alginic acid, dextrin, maltodextrin, methylcellulose, ethyl cellulose, hydroxyethyl cellulose, hydroxypropyl cellulose, hydroxypropyl methylcellulose, carboxymethyl cellulose sodium, povidone, pregelatinized starch and starch.

5. The pharmaceutical dosage form according to claim 1, in the form of tablets or capsules.

6. The pharmaceutical dosage form according to claim 1, comprising:
(a) from about 10 to 60% by weight Cinacalcet or its pharmaceutically acceptable salts;
(b) from about 20.0 to 80.0% by weight of one or more diluents; and (c) from about 1.0% to 8.0% by weight of one or more binders.

* * * * *